(12) United States Patent
Masterson et al.

(10) Patent No.: US 6,200,550 B1
(45) Date of Patent: Mar. 13, 2001

(54) ORAL CARE COMPOSITIONS COMPRISING COENZYME Q10

(75) Inventors: Robert V. Masterson, Vashon Island; Laura D. Manning, Kirkland, both of WA (US)

(73) Assignee: Q-pharma, Inc., Edmonds, WA (US)

( * ) Notice: Subject to any disclaimer, the term of this patent is extended or adjusted under 35 U.S.C. 154(b) by 0 days.

(21) Appl. No.: 09/210,180

(22) Filed: Dec. 11, 1998

(51) Int. Cl.$^7$ ............................... A61K 7/16; A61K 7/28
(52) U.S. Cl. ................................. 424/49; 424/50
(58) Field of Search ........................... 424/49–58

(56) References Cited

U.S. PATENT DOCUMENTS

| | | | |
|---|---|---|---|
| 3,488,419 | 1/1970 | McCune et al. | 424/49 |
| 3,538,230 | 11/1970 | Pader et al. | 424/50 |
| 3,934,002 | 1/1976 | Haefele | 424/54 |
| 3,937,807 | 2/1976 | Haefele | 424/52 |
| 4,599,363 | 7/1986 | Miles, Jr. et al. | 514/770 |
| 4,618,488 | 10/1986 | Maryama et al. | 424/49 |
| 4,654,373 | 3/1987 | Bartelli et al. | 514/690 |
| 4,701,319 | 10/1987 | Woo | 424/52 |
| 4,702,905 | 10/1987 | Mitchell et al. | 424/57 |
| 4,716,034 | 12/1987 | Schelm | 424/49 |
| 4,721,614 | 1/1988 | Winston et al. | 424/52 |
| 4,869,900 | 9/1989 | Pozzi et al. | 424/94.1 |
| 4,975,271 | 12/1990 | Dunn et al. | 424/50 |
| 5,032,384 | 7/1991 | Yeh et al. | 424/49 |
| 5,077,049 | 12/1991 | Dunn et al. | 424/426 |
| 5,188,817 | 2/1993 | Ozick | 424/49 |
| 5,278,201 | 1/1994 | Dunn et al. | 523/113 |
| 5,278,202 | 1/1994 | Dunn et al. | 523/113 |
| 5,487,897 | 1/1996 | Polson et al. | 424/426 |
| 5,925,335 | 7/1999 | Shuch et al. | 424/49 |

FOREIGN PATENT DOCUMENTS

| | | | |
|---|---|---|---|
| 93 01471 | * | 10/1994 | (SE) . |
| 9500610 | | 2/1995 | (SE) . |
| 86 04563 | * | 8/1986 | (WO) . |
| 95 05164 A1 | * | 2/1995 | (WO) . |
| 9714740 A1 | * | 4/1997 | (WO) . |
| 97 22333 A1 | * | 6/1997 | (WO) . |
| 98 08490 A1 | * | 3/1998 | (WO) . |
| 98 56336 A1 | * | 12/1998 | (WO) . |

OTHER PUBLICATIONS

U.S. 4654373 Itaf Bertelli/Ital Farmaco, Mar. 31, 1987.*
U.S. 4869900 Crenzii, Sep. 26, 1989.*
WO/PCT 94 15595 Hessel/Consult, Jul. 21, 1994.*
WO/PCT 94 06418 Dahlgren(II), Mar. 31, 1994.*
WO/PCT 97 36577 Amselem(I), Oct. 9, 1997.*
Folkers Koku Eisei Gakkai Zasshi 42(3):258–263, 1992.*
Shizukuishi et al Biomed. Res 4(1):32–40, 1983.*
Inoshita et al Biomed. Koku Eisei Gakkai Zasshi 32(2):139–146, 1982.*
Wilkinson et al III Biomed Clin Aspects Coenzyme Q Proc. Int. Symp. 1976:251–266, 1977.*
Hanioka et al Molecular aspects of Medicine 15 Suppl 5241–5248, 1994.*
Wilkinson eta II Research Communications in Chem. Pathol & Pharmacol 14(4)715–719, Aug. 1976.*
Wilkinson et al Research Communications in Chem. Pathol & Pharmacol 12(1):111–123, Sep. 1975.*
Iwamoto et al Research Communications in. Chem Pathol-.Pharmacol. 11(2):265–271, Jun. 1975.*
Watts British Dental Journal 178(6):209–213., Mar. 25, 1995.*
Littaru et al., *Proc. Natl. Acad. Sci. USA* 68:2332–2335 (1971).
McRee et al., *J. Dent. Health* 43:659–666 (1993).
Nakamura et al., *Int. J. Vit. Nutr. Res.* 43:84–92 (1973).

* cited by examiner

*Primary Examiner*—Shep K. Rose
(74) *Attorney, Agent, or Firm*—Townsend and Townsend and Crew LLP

(57) ABSTRACT

The present invention provides oral care compositions comprising high concentrations of Coenzyme $Q_{10}$ which are uniform, stable, and retain characteristics favorable to the consumer. The oral care compositions of the present invention include toothpastes and tooth gels, pastes, irragants, ointments, films, dental gels, mouth rinse, mouth spray, chewing gum, lozenges and a base composition for coating toothpicks and dental floss. In formulating the oral care compositions of the present invention, the Coenzyme $Q_{10}$ is solubilized in a non-toxic solubilizing agent which is compatible with use in the oral cavity. The formulations further comprise a water soluble flavoring agent. Methods are also provided for preparing the oral care compositions of the present invention.

5 Claims, No Drawings

ORAL CARE COMPOSITIONS COMPRISING COENZYME Q10

BACKGROUND OF THE INVENTION

The present invention relates to oral care compositions containing a solubilized and uniformly dispersed antioxidant. In particular, the antioxidant is ubiquinone (2,3-dimethoxy-3-methyl-6-decaprenyl-1,4-benzoquinone) otherwise designated, Coenzyme $Q_{10}$. Coenzyme $Q_{10}$ is a potent water insoluble antioxidant that is involved in electron transport and oxidative phosphorylation.

Oral care compositions include solutions, emulsions and devices that help maintain healthy teeth and gums for use by individuals and by dental professionals. These compositions include toothpastes, tooth gels, mouth rinse, oral sprays, pastes, ointments, films, dental gels, irragants, dental floss, and other related products that are designed for the maintenance and care of the oral cavity.

It is generally accepted that compositions designed to deliver an active substance, for example a drug, to a given tissue are more effective when the substance is solubilized and dispersed in a uniform manner. In the formulation of oral care compositions which are designed to last in the oral cavity for short periods of time, the availability of an active ingredient is particularly important. For example, toothpastes are generally used for less than two minutes for cleaning teeth. The delivery of active oral care ingredients, such as sodium fluoride, must be formulated in a manner to reach the desired target, e.g., teeth and gums, before it is removed from the oral cavity.

Dental studies in humans have demonstrated a deficiency of Coenzyme $Q_{10}$ in the gingiva tissues of individuals with gum disease (Littaru et al., *Proc. Natl. Acad. Sci. USA* 68:2332–2335 (1971), Nakamura et al., *Int. J. Vit. Natr. Res.* 43:84–92 (1973)). Clinical studies have shown that dietary supplementation with orally ingested formulations of Coenzyme $Q_{10}$ improved diseased gingiva tissues in adult humans (Wilkinson et al., *Res. Comm. Chem. Path. Pharm.* 13:715–719 (1976), Folkers, *J. Dent. Health* 42:258–263 (1992)). Also, a decrease in sub-gingival microbes has been observed following oral supplementation of Coenzyme $Q_{10}$ (McRee et al., *J. Dent. Health* 43:659–666 (1993)). These systemic formulations provide relatively low concentrations of Coenzyme $Q_{10}$ to the gingival tissues.

Coenzyme $Q_{10}$ has also been formulated as an oral care product to treat gingivitis. In one formulation, Coenzyme $Q_{10}$ was compounded for topical application in soybean oil. The composition was applied to periodontal pockets of receding gums by a dentist. In these studies there was an improvement in periodontal condition (Hanioka et al., *Mol. Aspects. Med.* 15:241–248 (1994).

Recently, oral care compositions comprising Coenzyme $Q_{10}$, including a toothpaste, have been disclosed in Swedish Patent publication No. 9500610-2. In these compositions soybean oil at about 2% was used as a solubilizing and encapsidizing agent. It has been determined that this amount of oil provides a product with unfavorable consumer characteristics, including an unattractive feel and taste.

In another formulation for an oral care product, Coenzyme $Q_{10}$ was combined with a protective colloid forming substance. The colloid forming substance was provided to protect the Coenzyme $Q_{10}$ from breakdown and to release the coenzyme upon contact with the environment of the oral cavity. As oral care compositions are present in the oral cavity for relatively brief periods of time. The time period required for release of the coenzyme from the colloid forming substance can reduce the amount of active coenzyme available to the gingiva.

It is common in the art when formulating oral care compositions to solubilize water-insoluble ingredients, e.g., Coenzyme $Q_{10}$, in natural essential oils used to flavor the composition. Commonly used oils include, for example, peppermint oil, spearmint oil, and the like. When formulated in this way the maximum quantity of water-insoluble ingredient which can be in the formulation is limited by the solubility of the ingredient in the essential oil. For example we have found that the higher concentration of Coenzyme $Q_{10}$ that can be added to the essential oil in the preparation of a toothpaste is about 0.05%. If a greater concentration of the ingredient is added, the product becomes unstable and the water-insoluble ingredients can precipitate or separate from the composition.

Previous oral care compositions have solubilized Coenzyme $Q_{10}$ in lipids, e.g., soybean oil, flax or bran seed oil, and the like in order to increase the amount Coenzyme $Q_{10}$ which can be added. The inherent oily characteristics of these formulations provides a commercial product having unfavorable consumer reaction. For example, in toothpaste, the high concentrations of, for example, soybean oil required to solubilize and encapsidize sufficient concentrations of Coenzyme $Q_{10}$ to be effective in treating or ameliorating the symptoms of gingivitis or periodontitis can provide a composition having an oily taste and feel in the oral cavity. Also, toothpaste preparations comprising high concentrations of oil can have a tendency to separate.

The tendency of water and oil phases of certain oral care formulation to separate can also be disadvantageous when an oral care composition is formulated as a mouth rinse, oral spray, dental gel or other formulation including a base composition for use in the coating used with dental floss or toothpicks. When formulated as a mouthwash, phase separation can occur such that the oil phase containing the Coenzyme $Q_{10}$ floats on top of the aqueous solution at a concentration of one or more parts per million. Solubilizing Coenzyme $Q_{10}$ in oil for the preparation of dental floss or a toothpick can result in a product which is oily to the taste and feel.

Surprisingly, the present invention provides compositions and methods for incorporating high concentrations of Coenzyme $Q_{10}$ which are effective to improve the condition of gingival tissues in oral care formulations without the problems of oil/water phase separation and without providing compositions which possess unfavorable taste and tactile characteristics.

SUMMARY OF THE INVENTION

The present invention provides oral care compositions for treating and ameliorating the symptoms of gingivitis and periodontal disease. The compositions provide uniform, stable, homogeneous oral care products having high concentrations of Coenzyme $Q_{10}$ without characteristics unfavorable to consumers. Methods for preparing the compositions of the present invention are also provided.

In one embodiment, the oral care compositions of the present invention comprise a toothpaste or tooth gel having Coenzyme $Q_{10}$ concentrations of from about 0.01% to about 4% and higher. These high concentrations of Coenzyme $Q_{10}$ are rendered soluble and stable by admixing the Coenzyme $Q_{10}$ in a non-toxic solubilizing agent which is compatible for use in the oral cavity.

In a preferred embodiment, the solubilizing agent is polysorbate-80, polysorbate-20 or MIGLYOL 840, and is present in an amount of about 0.01% to about 5% of the total composition weight. The toothpaste or tooth gel compositions of the present invention further comprise a water soluble flavoring agent which reduces the amount of water insoluble ingredients and allows for an increase in the concentration of Coenzyme $Q_{10}$ while maintaining the uniformity and stability of the toothpaste composition.

Toothpaste compositions of the present invention also comprise a polishing agent in an amount of from about 3 to about 70%, a surfactant in an amount of from about 0.1% to about 5%, a humectant in an amount of from about 10% to about 75%, a gelling agent in an amount of from about 0.5% to about 5%, and a sweetener. The toothpaste composition can further comprise anti-tartar agents, anticaries agents, antibacterials and can also comprise additional antioxidants. Antioxidants that are suitable for use in an oral care compositions of the present invention include tocopheryl acetate and β-carotene, and the like.

In another embodiment, the oral care composition can be formulated as a dental gel. A dental gel of the present invention comprises Coenzyme $Q_{10}$ in an amount of from about 0.01% to about 4% and a solubilizing agent in an amount of 0.01% to about 5% of the total compositions weight. The remainder of the composition comprises a surfactant in an amount of about 10%, a humectant in an amount of about 34%, a gelling agent in an amount of from about 0.5% to about 7%, a water soluble flavoring agent, and a sweetener in an amount of from about 0.1% to about 2% by weight. Dental gels of the present invention can further comprise additional antioxidants including tocopheryl acetate and β-carotene.

In still a further embodiment of the present invention, the oral care composition can be formulated as a mouth rinse comprising Coenzyme $Q_{10}$ in an amount of from about 0.01% to about 4% and a solubilizing agent in an amount of from about 0.01% to about 5%. The mouth rinse product of the present invention further comprises ethyl alcohol, a humectant, a sweetening agent, a flavoring agent and a bacterial agent. In a particularly preferred embodiment, the mouth rinse further comprises additional antioxidants, e.g., tocopheryl acetate and β-carotene.

In yet still another embodiment of the present invention, the oral care composition is formulated as a base used to coat, for example, a toothpick or dental floss. The base composition comprises from about 0.01% to about 4% by weight Coenzyme $Q_{10}$ solubilized in a solubilizing agent comprising a polyoxyethylene sorbitan monostearate, a polyethylene glycol, a non-ionic poloxamer surfactant, a polyethyleneglycolparaisooctyphenyl ester, a glycerol ester of a fractionated fatty acid having a chain length of 8 to 10 carbons. Ethyl alcohol, a flavoring agent and a sweetening agent comprise the remainder of the composition.

DESCRIPTION OF THE SPECIFIC EMBODIMENTS

The present invention describes compositions and methods for solubilizing therapeutically effective concentrations of Coenzyme $Q_{10}$ in oral care formulations for treating gingivitis and periodontitis. The compositions provide for formulations having between 0.01% and 20% Coenzyme $Q_{10}$ when formulated as a toothpaste, tooth gel, dental gel, mouth rinse, oral spray, paste, ointment, irragant, films or as a base substance for coating toothpicks or dental floss. Particularly preferred formulations comprise more than 0.05% Coenzyme $Q_{10}$. Thus, the gingiva can receive an effective concentration of Coenzyme $Q_{10}$ that is uniform without characteristics that are negative to the consumer.

Oral care compositions generally include solutions, emulsions and devices that help maintain healthy teeth and gums. These compositions can include toothpastes, tooth gels, dental gels, mouth rinse, oral sprays, pastes, ointments, irragants, dental floss, toothpicks and the like. In the compositions and methods of the present invention, Coenzyme $Q_{10}$ is combined with a solubilizing agent and water soluble flavoring agents which are used to increase the concentration of Coenzyme $Q_{10}$ that can stably and uniformly be admixed in the formulations.

The compositions of the present invention comprise Coenzyme $Q_{10}$ combined with a solubilizing agent. As used in the present invention a solubilizing agent must be capable of fully solubilizing Coenzyme $Q_{10}$ in a water based oral care composition. Also, the solubilizing agent must be pharmaceutically acceptable, i.e., non-toxic to cells or tissues. The solubilizing agent of the present invention must also be capable of preventing Coenzyme $Q_{10}$ from precipitating from an oral care composition, and from forming a heterogeneous, unstable, composition which has unfavorable tactile and taste characteristics.

Preferred solubilizing agents for use in the present invention include, polyoxyethylene sorbitan monosterate (polysorbate-80, Tween-80) and other preparations of polyoxyethylene sorbitan monostearate including, e.g., polysorbate-20 (Tween-20), and related compounds. Other suitable solubilizing agents that can be used in the present invention include polyethylene glycols, non-ionic poloxamer surfactants, i.e., PLURONIC F108 (BASF Corp.), polyethylene-glycolparaisooctyphenyl ethers, (TRITON, Baker Chemical Company), glycerol esters of a fractionated fatty acid having a chain length of 8 to 10 carbons, i.e., MIGLYOL 829 (Huls America, Inc., Piscataway, N.J.), and propylene glycol diesters of a saturated fatty acid having a chain length of 8 to 10 carbons, i.e., MIGLYOL 840 (Huls America, Inc., Piscataway, N.J.). The solubilizing agent can be present in an amount from about 0.01% to about 5% by weight of the composition. It is particularly preferred that the solubilizing agent be polysorbate 80 and is present in an amount of from about 0.1% to about 1.5% by weight of the composition.

Coenzyme $Q_{10}$ is readily available and for example is manufactured by Kaneka Company, Osaka, Japan. It is also readily available from a number of other suppliers. Concentrations of from about 0.001% to about 20% Coenzyme $Q_{10}$ in a solubilizing agent of the present invention are preferred for making the oral care compositions of the present invention. When the oral care composition is formulated as a toothpaste a concentration of from about 0.001% to about 20% can be made which comprises uniform and stably dispersed Coenzyme $Q_{10}$ throughout the composition. Compositions having a Coenzyme $Q_{10}$ concentrations of from about 0.01% to about 4% are preferred embodiments of the present invention. Particularly preferred toothpaste compositions comprise from about 0.2% to about 1% Coenzyme $Q_{10}$.

Admixing Coenzyme $Q_{10}$ with the solubilizing agents of the present invention also allows for the preparation of other oral care compositions comprising high concentrations of Coenzyme $Q_{10}$. In particular, the present invention allows for the preparation of pastes, irragants, gels, films and ointments for use in the oral cavity to provide compositions which slowly release an active ingredient over an extended period of time to treat or ameliorate the symptoms of gingivitis and/or periodontitis. The concentration of Coenzyme $Q_{10}$ preferred in these compositions can be from between about 0.001% to about 4%. These compositions can also include other active ingredients, such as, antibacterials, growth factors, bone morphogenic protein, anti-inflammatory agents, and the like.

Oral care formulations compounded as dental gels comprise Coenzyme $Q_{10}$ at concentrations of from about 0.001% to about 4%. Dental gels which comprise from about 0.1 to about 2.5% are preferred, and from about 0.5% to about 2% are particularly preferred. When the oral care product is formulated as a mouth rinse a Coenzyme $Q_{10}$ concentration of from about 0.001% to 2% can be useful. A concentration of from about 0.01% to 1% is preferred, and from about 0.05% to about 0.5% is particularly preferred. Oral care compositions can also be formulated as a base composition for coating a toothpick or dental floss. The base composition of the present invention can comprise from about 0.01% to about 4% Coenzyme $Q_{10}$. It is preferred that the base composition comprise from about 0.1% to about 2% Coenzyme $_{10}$, and particularly preferred for the base composition to comprise from about 0.25% to 1% Coenzyme $Q_{10}$.

Toothpaste compositions generally contain polishing agents, surfactants, humectant, gelling agents, and other excipients such as flavoring and coloring agents. The polishing agent can be selected from any of those which are currently employed for the purpose of making dental preparations. Suitable examples are water-insoluble sodium or potassium metaphosphate, hydrated or anhydrous dicalcium phosphate, calcium pyrophosphate, zirconium silicate or mixtures thereof. Useful polishing agents include various forms of silica, especially silica xerogels such as those described in U.S. Pat. No. 3,538,230, incorporated herein by reference. Particularly preferred polishing agents include, for example, SYLOID silica gels (W. R. Grace Company) and ZEODENT silica gels (J. M. Huber Corporation). The polishing agent is generally finely divided, with a particle size smaller than 10 $\mu$m, for example, 2 to 6 $\mu$m. The polishing agent may be employed in an amount of 3% to 75% by weight of the toothpaste. Typically, toothpaste preparations will contain 15% to 35% of the polishing agent.

A suitable surfactant is normally included in the toothpaste preparation. The surfactant is typically a water-soluble non-soap synthetic organic detergent. Suitable detergents are the water-soluble salts of, i.e., a higher fatty acid monoglyceride monosulphates, higher alkyl sulphates, e.g., sodium lauryl sulphate, alkylarylsulphonates, e.g., sodium dodecylbenzene-sulfonates, and higher alkyl sulphoacetates, e.g., sodium lauryl sulphoacetate, and the like. In addition, there may be employed saturated higher aliphatic acyl amines of lower aliphatic amino carboxylic acids having carbon atoms in the acyl radical and in which the amino acid portion is derived from the lower aliphatic saturated monaminocarboxylic acids having 2 to 6 carbon atoms, such as fatty acid amides of glycine, sarcosine, alanine, 3-aminopopanoic acid and valine, in particular, the N-lauryl, myristoyl and palmitoyl sarcosineate compounds. Conventional non-ionic surfactants may also be included if desired. The surfactant is typically present in toothpaste composition of the present invention in an amount of from about 0.1% to about 5% by weight. In a particularly preferred embodiment, sodium lauryl sulfate is used in an amount from about 0.5% to about 20% by weight.

Typically the liquid portion of a toothpaste composition will comprise mainly water combined with a humectant. The humectant can be selected from glycerol, sorbitol, propylene glycol, polyethylene glycol 400, or the like, or mixtures thereof. In a typical toothpaste formulation of the present invention the humectant is present in an amount from about 10% to about 75% by weight. Preferred embodiments of the present invention comprise from about 25% to about 60% humectant, or comprise a mixture of humecants. An advantageous mixture preferred in the present invention is water and sorbitol.

A gelling agent, such as, a natural or synthetic gum or gum-like material (e.g., Irish Moss, polyethylene glycol 300, an alkali metal carboxymethyl cellulose, such as, sodium carboxymethyl cellulose) can be used. Other gums which can be used include gum tragacanth, xanthum gum, polyvinyl-pyrrolidine, and water soluble hydrophilic colloidal carboxyvinyl polymers, such as those sold under the tradenames of CARBOPOL 934 and CARBOPOL 940. Gelling agents are generally used in an amount of typically about 0.5% to 5% by weight of the toothpaste.

Flavoring and sweetening agents can also be added to the instant compositions. Preferable flavoring agents are water soluble, i.e., water soluble 'spearmint' flavor from International Flavor and Fragrances (IFF), and water soluble 'peppermint' flavor from Technology Flavors and Fragrances (TFF). Flavoring agents are generally used in toothpaste formulations at levels of from about 0.01 to 2% by weight. Commonly used sweeteners in the art are suitable for use in the formulations of the present invention. In particular, saccharin can be used in an amount of from about 0.01% to about 2% by weight. The preferred amount of saccharin is between about 0.1% and about 1% by weight. Alternative sweetening agents which can be used include, dextrose, sucrose, fructose, levulose, aspartame, sodium cyclamate, and the like.

Phosphorus-containing anticalculus agents and/or bisbiguanide antiplaque agents can also optionally be added to the compositions of the present invention. Phosphorus-containing anticalculus agents such as disodium ethane-1-hydroxy-1, 1-diphosphonate anticalculus agents such as disodium ethane-1-hydroxy-1, 1-diphosphonate and related materials are described more fully in McCune et al., U.S. Pat. No. 3,488,419, incorporated herein by reference. Bisbiguanide antiplaque agents such as cholorhexidine (1,6-bis [$N^5$-p-chlorophenyl-$N^1$-biguanido]-hexane), the soluble and insoluble salts thereof and related materials such as 1,2-bis-($N^5$-p-tri-fluoromethyl-phenyl-$N^1$-biguanido)ethane are described more fully in Haefele, U.S. Pat. No. 3,934,002, Haefele, U.S. Pat. No, 3,937,807, Belgium Patent No. 843, 244, published Dec. 22, 1976 and Belgian Patent No. 844,764. These patents are incorporated herein by reference in their entirety. If present, the optional anticalculus and/or antiplaque agents generally comprise from about 0.01% to 2.5% by weight of a toothpaste composition described herein.

The compositions of the present invention can also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride ($SnF_2KF$), sodium hexafluorostannate, stannous chlorofluoride, sodium fluorozirconate and sodium monofluorophosphate. These materials, which dissociate or release fluorine-containing ions in water, suitably may be present in an effective but non-toxic amount, usually within the range of about 0.01 to 1% by weight of the water soluble fluorine content thereof.

In addition the compositions of the present invention can contain an additional anti-oxidant or a compound which is effective in preventing oxidation to decrease damage done by free radicals to the oral cavity. Anti-oxidants suitable for use in the present invention must be safe for oral use.

Suitable antioxidants include, but are not limited to, tocopheryl acetate, β-carotene, ascorbic acid, and melatonin. Tocopheryl acetate and β-carotene are most preferred for use in the present invention and are used at a concentration of between about 0.1% to about 20%, preferably they are used between about 0.2% and about 2% by weight.

The toothpaste may also contain antibacterial agents in amounts of about 0.01–5%. Typical examples of such agents include sodium benzoate, benzoic acid, citric acid, sorbic acid, methyl- and propyl-parabens, and can also include guanidines, biguanides and amines such as:

$N^1$-(4-chlorobenzyl)-$N^5$-2,4-dichlorobenzyl) biguanide;

p-chlorophenyl biguanide;

4-chlorobenzyhydryl biguanide;

4-chlorobenzhydrylguanylurea;

n-3-lauroxypropyl-$N^5$-p-chlorobenzylbiguanide;

1,6-di p-chlorophenylbiguanidohexane;

1-(lauryldimethylammonium)-8-(p-chlorobenzyldimethylammonium) octane dichloride;

5,6-dichloro-2-guanidinobenzimidazole;

$N^1$-p-chlorophenyl-$N^5$-laurylbiguanide;

5-amino-1,3-bis(2-ethylhexyl)-5-methylhexahydropyrimidine; and their non-toxic acid addition salts.

Various other materials may be incorporated in the toothpaste preparations of this invention. Examples thereof include coloring or whitening agents, such as titanium IV oxide, preservatives, chlorophyll compounds, ammoniated materials, such as urea, diammoniumphosphate, and mixtures thereof, and other constituents. Each of these adjutants may be typically incorporated in the instant toothpastes in amounts up to about 5%. Other additional materials which may be used include healing agents, vasomotors and clotting agents, and the like, in amounts from about 0.01% to about 10%.

There are, of course, numerous examples of special toothpastes or dentrifices adapted for special purposes or with special advantages. Thus, e.g., EP 280077 describes a toothpaste which contains stabilized dicalcium phosphate dihydrate, resulting in a high water absorption capacity and an adequate viscosity at low abrasive content; U.S. Pat. No. 4,618,488 (incorporated herein by reference) discloses stable toothpastes, in particular transparent toothpastes, which contain amorphous silica and/or silicate abrasive with specific surface areas, resulting in long term stability of the transparency of the toothpaste; U.S. Pat. No. 4,721,614 (incorporated herein by reference) discloses a toothpaste which contains sodium bicarbonate as the sole abrasive, thus avoiding excessive abrasive properties and retaining a good storage stability; U.S. Pat. No. 4,702,905 and U.S. Pat. No. 4,716,034 (each incorporated herein by reference) disclose toothpastes which are resistant to syneresis in contact with polyolefin packaging, which toothpastes are thus suitable for packaging in e.g. laminate tubes, mechanical dispensers and flexible sachets; U.S. Pat. No. 4,599,363 (incorporated herein by reference) discloses a method for wetting and dispersing powders for toothpaste preparation in turbulent liquid medium, the method preventing formation of lumps and loss of powdered solids and resulting in high quality toothpaste compositions; U.S. Pat. No. 4,701,319 (incorporated herein by reference) discloses a toothpaste which has good stability, viscosity and processing properties, the toothpaste containing abrasive, carboxyvinyl polymer, and a carrageenan humectant. Each specialized toothpaste formulation is adaptable to the addition of Coenzyme $Q_{10}$ at concentration of over 0.05% and up to 6% using the methods of the present invention. The formulations of the present invention form stable homogeneous compositions with high concentrations of Coenzyme $Q_{10}$ uniformly dispersed throughout the composition.

Pastes, irragants, gels, films and ointments suitable for use in the present invention can comprise, for example, biodegradable polymers including crosslinked hydrolyzed gelatin, natural hydrophilic polymeric agents, such as, agar, algin, carrageenan, and the like, synthetic polymers, such as, chemically modified celluloses, polyvinyl alcohols, polyvinylpyrrolidone, polyacrylic acid derivatives, and the like. See, for example, U.S. Pat. Nos. 5,032,384, and 5,188,817, incorporated herein by reference. Various other biodegradable implants, applied as either an implant precursor or a complete implant, can also be used. See for example, U.S. Pat. Nos. 5,278,201, 5,278,202, 5,077,049, 5,487,897, and 4,975,271, each incorporated by reference herein in their entirety. It is particularly preferred that these compositions further comprise anti-inflammatory agents, anti-bacterial agents, bone morphogenic protein, growth factors, or other active agent beneficial to the treatment or amelioration of the symptoms of gingivitis and periodontitis.

The oral care compositions comprising high concentrations of Coenzyme $Q_{10}$ can also be formulated as a dental gel. A dental gel of the present invention comprises a surfactant, a humectant and a gelling agent. The gels of the present invention are preferred to be free from abrasives, analgesics, and substances that alter the flora balance of the oral cavity. Surfactants, humectant and gelling agents suitable for formulated dental gels are described above for the preparation of toothpaste compositions.

When the oral composition is in the form of an oral spray, the vehicle can be a hydroalcohol solution and the composition can also contain flavorings, peptizing agents, sweeteners, moistening agents or cooling agents, and the like.

The oral composition of the present invention can also be in the form of a mouth rinse, for example, the vehicle can essentially be constituted by an aqueous of alcohol solution of a foaming surfactant which may optionally contain a thickening agent, sweetening and flavoring agents. Optionally, the mouth rinse can also contain an bactericidal agent, anti-inflammatory agent, antiplaque agents, and the like.

The compositions of the present invention can also be formulated as a chewing gum or lozenge. In this form the compositions comprise at least one natural or synthetic chewable gum and can contain plasticizers, vitamins, aromatizing or palatabilizing agents, sugars, moistening agents, bactericidal agents, preservatives, dyes, and optionally polishing agents.

Examples of gums with sufficient elasticity to be chewed either on their own or as a mixture are natural gums, such as, Heva latex, chicle gum, schelong gum and synthetic gums, such as, polyvinyl acetate and various synthetic elastomers, including, silicone rubber and butyl rubber. In general, the gums comprise about 0.5% to about 70% by weight of the chewable gum. A particularly preferred formulation for a gum of the present invention comprises sorbital, a chewable gum as provided above, xylitol, water soluble artificial spearmint flavor, titanium dioxide, Coenzyme $Q_{10}$ (in a concentration from about 0.01% to about 2%), carnauba wax and bees wax.

Methods for preparing oral care compositions of the present invention comprise solubilizing Coenzyme $Q_{10}$ separately prior to adding to other ingredients of the formulation. It is typical that the solubilized Coenzyme $Q_{10}$ is then admixed with one or a mixture of any humectant used in the formulation. The remaining ingredients can be admixed prior to adding to the component containing Coenzyme $Q_{10}$. At each stage the components must be mixed thoroughly to form a uniform composition. It is particularly preferred in making a toothpaste or tooth gel formulation of the present invention to combine Coenzyme $Q_{10}$ with polysorbate-80. The Coenzyme $Q_{10}$ containing component is then admixed with a component comprising sorbitol, trisodium phosphate, sodium fluoride, CARBOPOL 940 and saccharine which has been well mixed. Xanththum gum SYLOID 74 and titanium IV oxide (not included for a tooth gel) is then added and the compound is mixed until a homogeneous creamy paste results. A mixture of sorbitol, flavoring, sodium lauryl sulfate and sodium dodecylbenzene sulphonate is then admixed with the Coenzyme $Q_{10}$ containing mixture. SYLOID 63 is mixed in thoroughly to form the final toothpaste. Methods for preparing the oral care compositions of the present invention generally comprise solubilizing the Coenzyme $Q_{10}$ prior to the addition to any other ingredients or combination of ingredients. By solubilizing Coenzyme $Q_{10}$ with the agents of the present invention, homogeneous, stable, uniform oral care compositions comprising high concentrations of Coenzyme $Q_{10}$ with favorable flavor and feel characteristic can be obtained.

The following examples are offered by way of illustration, not by way of limitation.

EXAMPLE 1

Example 1 provides a representative toothpaste formulation which is representative of compositions of the present invention.

|  | % wt |
|---|---|
| sorbitol (70% Solution) | 52.60 |
| SYLOID 74 | 13.00 |
| glycerol | 11.80 |
| water | 4.97 |
| PEG 300 | 5.00 |
| SYLOID 63 | 3.00 |
| flavor | 2.00 |
| sodium lauryl sulfate | 1.50 |
| tri-sodium phosphate | 1.19 |
| Coenzyme Q10 | 1.00 |
| sodium saccharin | 1.00 |
| xanthum gum | 0.60 |
| polysorbate-80 | 0.60 |
| titanium IV oxide | 0.60 |
| sodium dodecylbenzene sulphonate | 0.50 |
| CARBOPOL 940 | 0.30 |
| sodium fluoride | 0.24 |
| dye | 0.10 |

The method for preparing the composition described in Example 1 is as follows (100 gram amount):

Component A. 1.0 g of Coenzyme $Q_{10}$ was mixed together with 0.6 g polysorbate-80. Mixing was performed with magnetic stirring or propeller type devices commonly used in the compounding of oral care products (an example of a suitable mixer is a Hobart mixer device). This mixture was added to 11.80 g of glycerol and 5.00 g polyethylene glycol 300 (PEG). The mixture was heated to above 40° C. while gently mixing. Mixing continued until a uniform compound was obtained that did not contain visible Coenzyme $Q_{10}$ particles. Optionally, a sonification step can be added to decrease the amount of time to mix Component A. A Branson-type sonification device has been used at a low setting for this step. Homogenization using commonly available homogenization devices can also be used to combine the ingredients into a uniform compound.

Component B. 39.45 g of sorbitol (70% solution, remaining amount water), together with 1.19 g of tri-sodium phosphate, 0.24 g sodium fluoride (corresponding to 1000 ppm), 0.30 g CARBOPOL 940 and 1.00 g sodium saccharin were heated to 60° C. After thoroughly mixing and removing the heat source, the following ingredients were added with further mixing: 0.60 g xanthum gum, 13 g of SYLOID 74 and 0.6 g of titanium IV oxide. This compound was further mixed to a creamy paste.

Component C: 13.15 grams of sorbitol (70% solution as above) together with 2.00 g of water-soluble flavor (such as artificial water-soluble "Spearmint" flavor from IFF), 1.5 g sodium lauryl sulfate and 0.5 g sodium dodecylbenzene sulphonate were mixed together and then added to Component A. This combination was further mixed until smooth. 3.00 g of SYLOID 63 was then added and mixed until a creamy, smooth appearance was achieved.

Toothpaste formulations have been made as above using a water-insoluble essential oil as a flavoring agent (Hagelin & Company, Branchburg, N.J.). These formulations resulted in a composition werein Coenzyme $Q_{10}$ precipitated when present at a concentration over 0.05%. When higher concentrations of Coenzyme $Q_{10}$ the essential oil flavoring agent resulted in a heterogeneous composition were a phase separation between the oil and water soluble phases occurred. The compositions also tasted oily when higher amounts of essential oil flavoring agent where used to obtain a better tasting preparation. By phase separation it is meant that the flavor and Coenzyme $Q_{10}$ formed a distinct portion in a heterogeneous system which separated from the toothpaste composition. The use of oil-based flavoring agent to solubilize high concentrations of Coenzyme $Q_{10}$ resulted in a composition which was heterogeneous and had an unfavorable taste and tactile feel at concentrations of Coenzyme $Q_{10}$ over 0.05% of the total composition weight.

Compositions were also made using another water-insoluble "Spearmint" flavor containing essential oils (International Flavors and Fragrances, Inc., New York, N.Y.; IFF) combined with Coenzyme $Q_{10}$ solubilized in oil. This composition also resulted in a phase separation when the flavoring was used in amounts that resulted in a better tasting toothpaste composition.

In contrast, compositions comprising the artificial water-soluble "Spearmint" flavor from IFF (International Flavor and Fragrances) used in the amounts given above provided excellent taste without a phase separation and the precipitation of Coenzyme $Q_{10}$. While this is a preferred flavoring agent for preparing oral care compositions of the present invention, other water-soluble, non-essential oil flavoring agents can also be used. For example, a water-soluble "Peppermint" flavor (Technology Flavors and Fragrances, Inc.) exhibited suitable flavor qualities when compounded into the toothpaste formulation described above.

Furthermore, it is optional to add a small quantity of water-insoluble flavoring agent, such as an essential oil, to the composition above. However, the amount of such an oil-based flavoring agent must be limited so as not to result in a phase separation or the precipitation of Coenzyme $Q_{10}$.

EXAMPLE 2

Example 2 provides a representative toothpaste composition of the present invention which further comprises zinc citrate as a tarter control substance and also includes additional antioxidants (tocopheryl acetate and β-carotene).

| | % wt |
|---|---|
| sorbitol (70% Solution) | 51.20 |
| SYLOID 74 | 13.00 |
| glycerol | 11.80 |
| water | 2.97 |
| PEG 300 | 5.00 |
| SYLOID 63 | 3.00 |
| zinc citrate | 2.00 |
| flavor | 2.00 |
| sodium lauryl sulfate | 2.00 |
| polysorbate-80 | 1.20 |
| tri-sodium phosphate | 1.19 |
| Coenzyme Q10 | 1.00 |
| sodium saccharin | 1.00 |
| xanthum gum | 0.60 |
| titanium IV oxide | 0.60 |
| tocopheryl acetate | 0.50 |
| β-carotene | 0.30 |
| CARBOPOL 940 | 0.30 |
| sodium fluoride | 0.24 |
| dye | 0.10 |

EXAMPLE 3

Example 3 provides a representative toothpaste gel composition of the present invention. This gel composition constitutes an oral care product formulation which is the same as Example 2 except it does not contain titanium IV oxide.

| | % wt |
|---|---|
| sorbitol (70% Solution) | 52.00 |
| SYLOID 74 | 13.00 |
| glycerol | 11.80 |
| water | 5.57 |
| PEG 300 | 5.00 |
| SYLOID 63 | 3.00 |
| flavor | 2.00 |
| sodium lauryl sulfate | 2.00 |
| polysorbate-80 | 0.60 |
| tri-sodium phosphate | 1.19 |
| Coenzyme Q10 | 1.00 |
| sodium saccharin | 1.00 |
| xanthum gum | 0.60 |
| CARBOPOL 940 | 0.30 |
| sodium fluoride | 0.24 |
| dye | 0.10 |

EXAMPLE 4

Example 4 provides a dental gel composition which is a representative composition of this present invention. This dental gel is suitable for application to the gums and teeth of a patient by a dental professional in a dental cup or tray.

| | % wt |
|---|---|
| water | 44.13 |
| sorbitol (70% Solution) | 34.00 |
| polypropylene glycol | 10.00 |
| glycerol | 5.00 |
| polysorbate-80 | 2.00 |
| Coenzyme Q10 | 2.00 |

-continued

| | % wt |
|---|---|
| CARBOPOL 940 | 1.00 |
| sodium hydroxide | 0.85 |
| flavor | 0.40 |
| citric acid | 0.17 |
| sorbic acid | 0.15 |
| methyl paraben | 0.15 |
| sodium saccharin | 0.10 |
| propyl paraben | 0.05 |

The method for preparing the composition described in Example 5 was as follows (100 gram amount): Component A. 2.00 g of Coenzyme $Q_{10}$ was mixed together with 10.00 g propylene glycol, 5.00 g glycerol and 2.00 g polysorbate-80. Component B. The following were heated to 60° C. while blended together: water, sorbitol, flavor (water-soluble), citric acid, methyl paraben, propyl paraben and sodium saccharin (in the corresponding amounts shown above). Component C: 1.00 g Carbopol 940. Component B was added to Component A and thoroughly mixed. Then Component C was added with mixing and the pH was adjusted to 5.5 (±5%).

EXAMPLE 5

Example 5 provides a representative dental gel composition of the present invention wherein the composition further comprises additional antioxidants (tocopheryl acetate and β-carotene).

| | % wt |
|---|---|
| water | 44.15 |
| sorbitol (70% Solution) | 33.20 |
| polypropylene glycol | 10.00 |
| glycerol | 5.00 |
| polysorbate-80 | 2.00 |
| Coenzyme Q10 | 2.00 |
| CARBOPOL 940 | 1.00 |
| sodium hydroxide | 0.85 |
| tocopheryl acetate | 0.50 |
| β-carotene | 0.30 |
| flavor | 0.40 |
| citric acid | 0.30 |
| methyl paraben | 0.15 |
| sodium saccharin | 0.10 |
| propyl paraben | 0.05 |

The method for preparing the composition of Example was as follows (100 gram amount): Component A. 2.00 g of Coenzyme $Q_{10}$ was mixed together with 10.00 g propylene glycol, 5.00 g glycerol and 2.00 g polysorbate-80. Component B. The following were heated to 60° C. while blended together: water, sorbitol, flavor (water-soluble), citric acid, methyl paraben, propyl paraben and sodium saccharin (in the corresponding amounts shown above). Component C: 1.00 g CARBOPOL 940, tocopheryl acetate and β-carotene are mixed together. Component B was added to Component A and mixed thoroughly, then Component C was added with mixing. The pH of the final compound was adjusted to 5.5 (±5%) with sodium hydroxide.

EXAMPLE 6

Example 6 provides a representative mouth rinse of the present invention. The mouth rinse formulations presented in Examples 7 and 8 provide further embodiments of mouth rinses of the present invention which comprise different amounts of ethyl alcohol.

| | % wt |
|---|---|
| water | 67.83 |
| alcohol (ethyl alcohol, 190 proof USP) | 15.00 |
| glycerol | 8.40 |
| sodium benzoate | 4.00 |
| sodium citrate | 2.00 |
| polysorbate-80 | 1.20 |
| sodium saccharin | 1.00 |
| flavor | 0.50 |
| Coenzyme Q10 | 0.05 |
| color | 0.01 |
| sodium hydroxide | 0.01 |

The method for preparing the composition described in Example 6 was as follows (100 gram amount): 8.4 g of glycerol was heated to 100° C. 67.83 g of water was heated to 80° C. and then add to the heated glycerol. While cooling 4.00 g of sodium benzoate was added with 2.00 g sodium citrate, 2.0 g water-soluble flavor (such as water-soluble spearmint flavor from TFF), and 1.0 g sodium saccharin. The mixture was allowed to cool to below 40° C. and then 15.00 g of ethyl alcohol was added. The following combination of ingredients was then added and mixed thoroughly: 0.05 g Coenzyme $Q_{10}$ and 1.20 g polysorbate-80.

EXAMPLE 7

Example 7 provides an alternative formulation for a mouth rinse of the present invention.

| | % wt/volume |
|---|---|
| water | 74.83 |
| alcohol (ethyl alcohol, 190 proof USP) | 10.00 |
| glycerol | 8.40 |
| sodium benzoate | 4.00 |
| polysorbate-80 | 1.20 |
| sodium saccharin | 1.00 |
| flavor | 0.50 |
| Coenzyme Q10 | 0.05 |
| color | 0.01 |
| benzoic acid | 0.01 |

EXAMPLE 8

Example 8 provides a third alternative formulation for a mouth rinse having additional antioxidants.

| | % wt |
|---|---|
| water | 76.04 |
| glycerol | 8.40 |
| alcohol (ethyl alcohol, 190 proof USP) | 5.00 |
| sodium benzoate | 4.00 |
| benzoic acid | 2.00 |
| polysorbate-80 | 1.20 |
| citric acid | 1.00 |
| sodium saccharin | 1.00 |
| flavor | 0.50 |
| tocopheryl acetate | 0.50 |
| (β-carotene | 0.30 |
| Coenzyme Q10 | 0.05 |
| color | 0.01 |

EXAMPLE 9

Example 9 provides a representative formulation for an oral spray of the present invention.

| | % wt |
|---|---|
| water | 82.81 |
| glycerol | 15.00 |
| Coenzyme Q10 | 1.00 |
| polysorbate-80 | 0.67 |
| folic acid | 0.17 |
| potassium sorbate | 0.15 |
| citric acid | 0.12 |
| flavor | 0.08 |

The method for preparing the composition described in Example 9 was as follows (100 gram amount): 1.00 g of Coenzyme $Q_{10}$ was mixed together with 15 g glycerol and 0.67 g polysorbate 80. This mixture was added to a mixture containing water, folic acid, potassium sorbate, citric acid and flavor (in the amount ratios shown above).

EXAMPLE 10

Example 10 provides a representative oral spray formulation of the present invention comprising additional antioxidants.

| | % wt |
|---|---|
| Water | 76.47 |
| glycerol | 12.00 |
| Coenzyme Q10 | 1.00 |
| polysorbate-80 | 0.67 |
| tocopheryl acetate | 0.50 |
| β-carotene | 0.30 |
| folic acid | 0.17 |
| potassium sorbate | 0.15 |
| citric acid | 0.12 |
| flavor | 0.08 |

The method for preparing the composition described in Example 10 was as follows (100 gram amount): 1.00 g of Coenzyme $Q_{10}$ was mixed together with 15 g glycerol and 0.67 g polysorbate-80. This combination was then added to another mixture containing water, tocopheryl acetate, β-carotene, folic acid, potassium sorbate, citric acid and flavor (in the corresponding amounts shown above).

EXAMPLE 11

Example 11 provides a representative base composition for the preparation of dental floss and toothpick products of the present invention.

| | % wt |
|---|---|
| alcohol (ethyl alcohol, 190 proof USP) | 96.70 |
| polysorbate-80 | 1.20 |
| Coenzyme Q10 | 1.00 |
| flavor | 0.60 |
| sodium saccharin | 0.40 |
| color | 0.10 |

The method for preparing the composition described in Example 11 was as follows (100 gram amount): 1.00 g of Coenzyme $Q_{10}$ was mixed together with 1.20 g of polysorbate-80. This mixture was added to a composition of 96.70 g ethyl alcohol, 0.60 g of flavor (water-soluble spearmint powder, IFF), and 0.40 g sodium saccharin. The addition of FD&C dyes can be added as an option (when add, 0.1 g was used).

Dental floss or toothpicks were soaked in the above base composition for 30 min and then were allowed to dry.

EXAMPLE 12

Example 12 provides a representative base composition for use in dental gums and lozenges (10X strength, use 1X in final composition) of the present invention.

| | % wt |
|---|---|
| sorbitol | 50.00 |
| glycerin | 24.50 |
| flavor | 18.00 |
| polysorbate-80 | 4.00 |
| PEG 300 | 3.00 |
| sodium saccharin | 3.00 |
| color | 1.00 |
| Coenzyme Q10 | 0.50 |

The method for preparing the composition described in Example 12 was as follows (100 gram amount): 24.50 g of glycerol and 50 g of sorbitol (70% solution, remaining amount is water) were heated together to 65° C. The mixture was removed from the heat source and the following ingredients were added: 18.00 g of water-soluble flavor (such as water-soluble spearmint flavor from TFF), 3.00 g polyethylene glycol 300 (PEG), 3.00 g sodium saccharin, 1.00 g color (FD&C dyes). After mixing a mixture of 0.50 g Coenzyme $Q_{10}$ and 4.00 g of polysorbate 80 was added and thoroughly mixed.

Although the foregoing invention has been described in some detail by way of illustration and example for purposes of clarity of understanding, it will be obvious that certain changes and modifications may be practiced within the scope of the appended claims.

What is claimed is:

1. A toothpaste composition comprising Coenzyme Q10 in an amount of from about 0.01% to about 4%, polysorbate 80 in an amount of from about 0.1% to about 1.5%, a SYLOID silica gel in an amount of from about 15% to about 35%, sodium lauryl sulfate in amount of about 1.5%, sodium dodecylbenzene sulphonate in an amount of about 0.5%, a mixture of sorbitol and glycerol in an amount of from about 25% to about 60%, a mixture of a water soluble hydrophilic colloidal carboxyvinyl polymer, xanthum gum and a polyethylene glycol in an amount of from about 0.5% to about 7%, water soluble flavoring in an amount of about 2%, sodium fluoride in an amount of about 0.24% and sodium saccharin in amount of about 1%.

2. The composition of claim 1, comprising Coenzyme Q10 in an amount of from about 0.01% to about 4%, polysorbate-80 in an amount of from about 0.1% to about 1.5%, a SYLOID silica gel in an amount of from about 15% to about 35%, sodium lauryl sulfate in amount of about 1.5%, sodium dodecylbenzene sulphonate in an amount of about 0.5%, a mixture of sorbitol and glycerol in an amount of from about 25% to about 60%, a mixture of a water soluble hydrophilic colloidal carboxyvinyl polymer, xanthum gum and a polyethylene glycol in an amount of from about 0.5% to about 7%, water soluble flavoring in an amount of about 2%, titanium oxide in an amount of up to about 5%, sodium fluoride in an amount of about 0.24% and sodium saccharin in amount of about 1%.

3. The composition of claim 2, further comprising an antitarter substance and an additional antioxidant.

4. The composition of claim 3, wherein the antitarter substance is zinc citrate.

5. The composition of claim 3, wherein the antioxidant is tocopheryl acetate and β-carotene.

* * * * *